US00PP19411P2

(12) United States Plant Patent
Nakanishi

(10) Patent No.: US PP19,411 P2
(45) Date of Patent: Nov. 4, 2008

(54) *PETUNIA* PLANT NAMED 'KUMIYAMA 1 GOU'

(50) Latin Name: *Petunia×hybrida*
Varietal Denomination: Kumiyama 1 Gou

(75) Inventor: Yoshiharu Nakanishi, Kyoto (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/700,681

(22) Filed: Jan. 30, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Petunia* plant named 'Kumiyama 1 Gou', characterized by its compact, upright and mounding plant habit; freely branching and flowering plant habit; and medium-sized purple-colored flowers with light green-colored petal margins.

1 Drawing Sheet

Botanical designation: *Petunia×hybrida.*
Cultivar denomination: 'Kumiyama 1 Gou'.

BACKGROUND OF THE INVENTION

The present invention relates to a new and distinct cultivar of *Petunia,* botanically known as *Petunia×hybrida* and hereinafter referred to by the name 'Kumiyama 1 Gou'.

The new *Petunia* is a naturally-occurring whole plant mutation of a proprietary selection of *Petunia×hybrida* identified as code number NA-15, not patented. The new *Petunia* was discovered and selected by the Inventor in April, 2003, as a single flowering plant within a population of plants of the parent selection in a controlled environment in Kyoto, Japan.

Asexual reproduction of the new *Petunia* by terminal cuttings in a controlled environment in Kyoto, Japan since April, 2004, has shown that the unique features of this new *Petunia* are stable and reproduced true to type in successive generations.

SUMMARY OF THE INVENTION

The cultivar Kumiyama 1 Gou has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kumiyama 1 Gou'. These characteristics in combination distinguish 'Kumiyama 1 Gou' as a new and distinct cultivar of *Petunia:*

1. Compact, upright and mounding plant habit.
2. Freely branching and flowering plant habit.
3. Medium-sized purple-colored flowers with light green-colored petal margins.

Plants of the new *Petunia* can be compared to plants of the parent selection. Plants of the new *Petunia* differ from plants of the parent selection in the following characteristics:

1. Plants of the new *Petunia* have smaller flowers than plants of the parent selection.
2. Plants of the new *Petunia* and the parent selection differ in flower color as petals of flowers of the parent selection do not have light green-colored margins.
3. Plants of the new *Petunia* are more rain tolerant than plants of the parent selection.

Plants of the new *Petunia* can also be compared to plants of the cultivar Rondo Violet Improved, not patented. In side-by-side comparisons conducted in Kyoto, Japan, plants of the new *Petunia* and the cultivar Rondo Violet Improved differed in the following characteristics:

1. Plants of the new *Petunia* were more vigorous than plants of the cultivar Rondo Violet Improved.
2. Plants of the new *Petunia* had thicker stems than plants of the cultivar Rondo Violet Improved.
3. Plants of the new *Petunia* had larger flowers than plants of the cultivar Rondo Violet Improved.
4. Plants of the new *Petunia* and the cultivar Rondo Violet Improved differed in flower color as petals of flowers of the cultivar Rondo Violet Improved did not have light green-colored margins.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Kumiyama 1 Gou' grown in a container.

The photograph at the bottom of the sheet comprises a close-up view of a typical flower of 'Kumiyama 1 Gou'.

DETAILED BOTANICAL DESCRIPTION

The photographs and following observations, measurements and values describe plants grown in Shiga, Japan, under commercial practice during the spring in a polyethylene-covered greenhouse. During the production of the plants, day temperatures averaged 23° C. and night temperatures averaged 13° C. Plants were grown for about four months with one plant per 13.5-cm container. In the following description, color references are made to The Royal Horticultural Society Colour Chart, 2001 Edition, except where general terms of ordinary dictionary significance are used.

Botanical classification: *Petunia×hybrida* cultivar Kumiyama 1 Gou.

Parentage: Naturally-occurring whole plant mutation of a proprietary selection of *Petunia×hybrida* identified as code number NA-15, not patented.

Propagation:

*Type.*—By terminal cuttings.

*Time to initiate roots.*—About one week at 20° C. to 25° C.

*Time to produce a rooted young plant.*—About three weeks at 20° C. to 25° C.

*Root description.*—Fine, fibrous; light brown in color.

*Rooting habit.*—Freely branching.

Plant description:

*Plant and growth habit.*—Compact, upright and mounding plant habit. Freely branching; about eight lateral branches develop per plant. Vigorous growth habit.

*Plant height.*—About 20 cm.

*Plant diameter.*—About 25 cm.

Lateral branch description:

*Length.*—About 8.3 cm.

*Diameter.*—About 3.2 mm.

*Internode length.*—About 2.7 cm.

*Strength.*—Strong.

*Aspect.*—Initially upright to outward.

*Texture.*—Pubescent.

*Color.*—144A.

Foliage description:

*Arrangement.*—Before flowering, alternate, simple; after flowering, opposite, simple; sessile.

*Length.*—About 4.4 cm.

*Width.*—About 3 cm.

*Shape.*—Elliptic to obovate.

*Apex.*—Obtuse.

*Base.*—Obtuse.

*Margin.*—Entire.

*Texture, upper and lower surfaces.*—Pubescent.

*Venation pattern.*—Pinnate; reticulate.

*Color.*—Developing foliage, upper and lower surfaces: 137C. Fully expanded foliage, upper surface: 137B; venation, 144B. Fully expanded foliage, lower surface: 146B; venation, 144B.

Flower description:

*Flower arrangement and habit.*—Single salverform flowers arising from upper leaf axils. Freely flowering habit with usually about 28 flowers developing per plant. Flowers not persistent. Flowers face upright or outwardly. Flowers fragrant.

*Natural flowering season.*—Plants of the new *Petunia* initiate and develop flowers about two or three weeks after planting. Long flowering period; flowering commences naturally during the spring and plants flower continuously throughout the summer until the fall in Japan; flowering continuous.

*Flower longevity.*—Individual flowers last about five days on the plant.

*Flower diameter.*—About 5 cm.

*Flower length (depth).*—About 3.9 cm.

*Tube diameter.*—About 6.4 mm.

*Flower bud.*—Shape: Cylindrical. Length: About 3.4 cm. Diameter: About 8.7 mm. Color: 79B; towards the apex, 144C.

*Corolla.*—Arrangement: Five petals fused at the base and opening into a flared trumpet. Petal length from throat: About 2.5 cm. Petal width: About 2.9 cm. Petal shape: Broadly obovate. Petal apex: Obtuse. Petal margin: Entire; slightly undulate. Petal texture, upper and lower surfaces: Smooth, glabrous; velvety. Tube texture: Pubescent. Color: Petals, when opening and fully opened, upper surface: 86A; towards the margins, 144C; venation, 90B. Petals, when opening and fully opened, lower surface: 86B; towards the margins, 144B. Throat: N79B. Tube: N92A.

*Calyx.*—Arrangement: One star-shaped calyx tube with five sepals fused at the base per flower. Sepal length: About 1.1 cm. Sepal width: About 3 mm. Sepal shape: Elliptic. Sepal apex: Rounded. Sepal margin: Entire. Sepal texture, upper and lower surfaces: Pubescent. Color, upper and lower surfaces: 137C.

*Peduncles.*—Length: About 3.3 cm. Diameter: About 1.9 mm. Angle: About 45° from vertical. Strength: Strong. Texture: Pubescent; viscid. Color: 144A.

*Reproductive organs.*—Stamens: Quantity/arrangement: Five per flower. Stamen length: About 1.5 cm to 2.3 cm. Anther shape: Ellipsoidal. Anther size: About 2 mm by 3 mm. Anther color: 79C. Pollen amount: Moderate. Pollen color: 188A. Pistils: Quantity: One per flower. Pistil length: About 2.6 cm. Style color: 145C. Stigma shape: Transversely ellipsoidal. Stigma color: 144A. Ovary color: 145A.

*Seed/fruit.*—Seed and fruit development have not been observed on plants of the new *Petunia*.

Temperature tolerance: Plants of the new *Petunia* have been observed to tolerate temperatures from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Kumiyama 1 Gou' as illustrated and described.

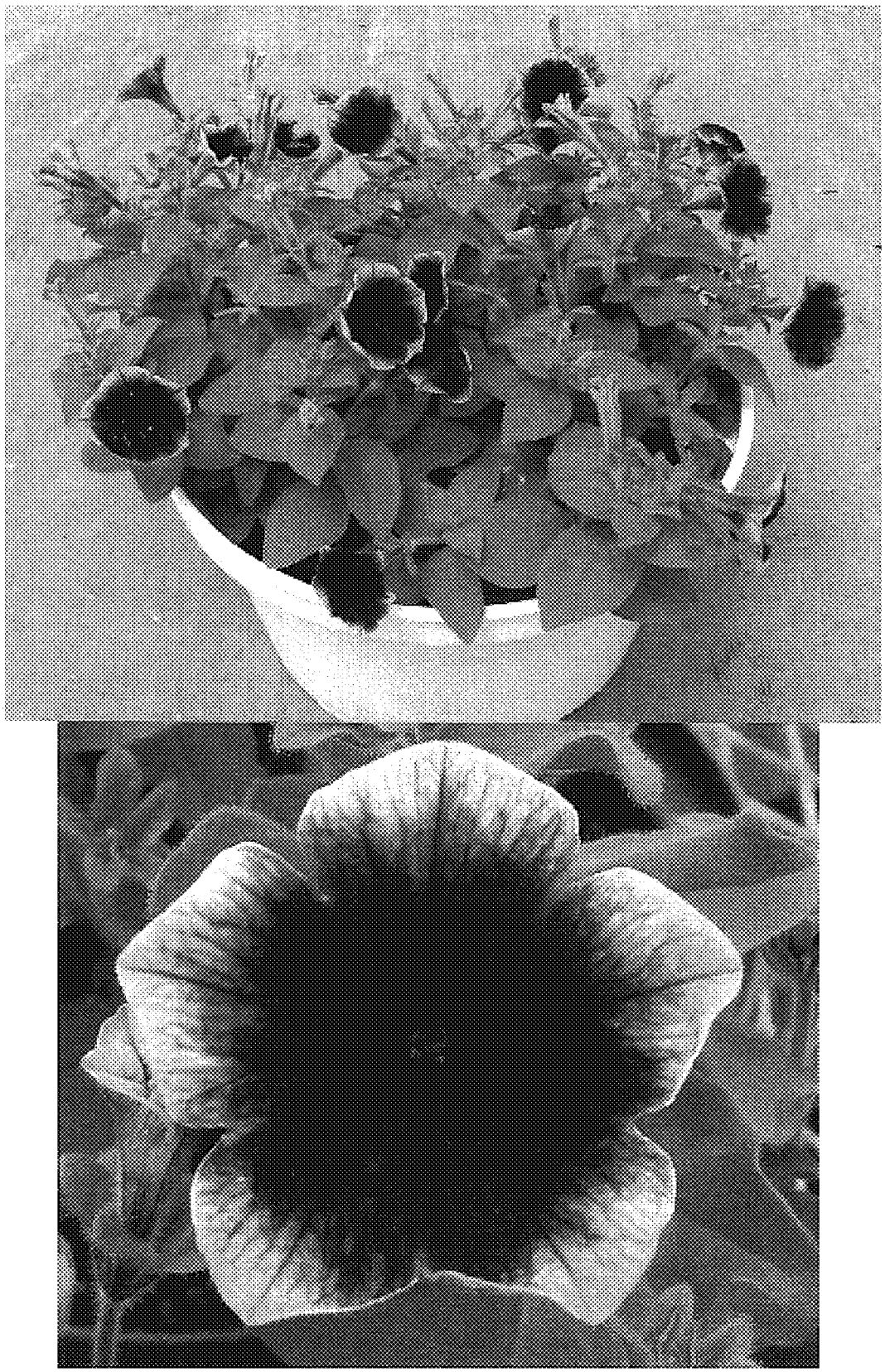

* * * * *